United States Patent [19]

Klein et al.

[11] Patent Number: 4,990,687

[45] Date of Patent: Feb. 5, 1991

[54] PREPARATION OF 4-METHYL-2-CYCLOHEXYLPHENOL

[75] Inventors: Alfons Klein, Duesseldorf; Helmut Fiege, Leverkusen; Lothar Puppe, Burscheid; Werner Jeblick, Leverkusen, all of Fed. Rep. of Germany

[73] Assignee: Bayer Aktiengesellschaft, Leverkusen, Fed. Rep. of Germany

[21] Appl. No.: 436,156

[22] Filed: Nov. 13, 1989

[30] Foreign Application Priority Data

Nov. 25, 1988 [DE] Fed. Rep. of Germany ....... 3839853

[51] Int. Cl.$^5$ ...................... C07C 39/17; C07C 37/11
[52] U.S. Cl. ...................................... 568/743; 568/734
[58] Field of Search ................ 568/743, 789, 794, 734

[56] References Cited

U.S. PATENT DOCUMENTS

| 1,917,823 | 7/0019 | Britton et al. | 568/743 |
|---|---|---|---|
| 4,283,573 | 8/1981 | Young | 568/794 |
| 4,329,509 | 11/1982 | Haag et al. | 568/768 |
| 4,391,998 | 7/1983 | Wu | 568/794 |
| 4,927,979 | 5/1990 | Yamagishi et al. | 568/794 |

FOREIGN PATENT DOCUMENTS

| 2437322 | 4/1975 | Fed. Rep. of Germany | 568/790 |
|---|---|---|---|
| 0095951 | 8/1978 | Japan | 568/743 |
| 1917823 | 7/1933 | United Kingdom | 568/743 |
| 731270 | 6/1955 | United Kingdom | 568/736 |
| 802884 | 10/1958 | United Kingdom | 568/743 |
| 998186 | 7/1965 | United Kingdom | 502/20 |

OTHER PUBLICATIONS

European Search Report.
Journal of Applied Chemistry of the USSR; vol. 41, No. 2, Feb. 1968.
Beilsteins Handbuch der Organischen Chemie; 1966.

Primary Examiner—Werren B. Lone
Attorney, Agent, or Firm—Sprung Horn Kramer & Woods

[57] ABSTRACT

4-Methyl-2-cyclohexylphenol can be prepared by alkylation of p-cresol with cyclohexanol or cyclohexene by performing the reaction in the liquid phase in the presence of 1–10% by weight, based on the amount of p-cresol, of a large pore, acidic zeolite.

17 Claims, No Drawings

PREPARATION OF 4-METHYL-2-CYCLOHEXYLPHENOL

BACKGROUND OF THE INVENTION

1. Field of the Invention

The invention relates to a process for preparing 4-methyl-2-cyclohexylphenol from p-cresol and cyclohexanol or cyclohexene.

4-Methyl-2-cyclohexylphenol is used for preparing stabilizers for thermoplastics and elastomers (DE-A-3,021,726).

2. Description of the Related Art

4-Methyl-2-cyclohexylphenol can be prepared in "moderate" yield (no further information given) by reacting p-cresol with cyclohexanol in 72% strength sulphuric acid at 60° C. (J. Prakt. Chem. N.F. 159 (1941), 155, especially 164).

It has also become known to catalyse this reaction with aluminum chloride or phosphoric acid (Zh. Organ. Khim. 1 (1965), 510 of the English translation).

In both cases the reaction is carried out at 90°–100° C.; in the case of AlCl$_3$, an equimolar amount of catalyst but 5 times the molar amount of p-cresol, based on the cyclohexanol, is used, and the catalyst is added to the mixture of the reactants. In the case of phosphoric acid, it is introduced first in a 3 times molar excess over the p-cresol together with the latter, and an amount of cyclohexanol which is equimolar to the p-cresol is then added. The yields are reported as 61% (AlCl$_3$) and 78% (H$_3$PO$_4$).

Zh. Prikl. Khim. 41 (2) (1968), 381 of the English translation, describes the reaction of p-cresol with cyclohexene in the presence of acidic ion exchangers. This reaction always produces, even with an excess of p-cresol, a substantial proportion of cyclohexyldisubstituted p-cresol. In addition, considerable amounts of cyclohexyl p-tolyl ether are formed. If the alkylation is carried out with cyclohexanol under such conditions, the predominant reaction product is cyclohexyl p-tolyl ether.

Furthermore, U.S. Pat. No. 1,917,823 discloses reacting phenol and o-cresol with cyclohexene or cyclohexanol in the presence of bleaching earths. This reaction is in every case carried out under high temperatures and superatmospheric pressure. According to this U.S. Patent, the alkylation in the ortho position is not the final substitution position; on the contrary, the ortho product is converted into the para product by the higher reaction temperatures; if o-cyclohexylphenol is added at the start, even the further formation of this product is suppressed.

In DE-A-2,437,322, the catalysts used for the alkylation by means of alkenes are molecular sieves. However, in this reaction the phenolic reactant used is m-cresol, which in a first stage is easily converted into a mixture of the various isomeric alkyl-m-cresols which, in a second step, produce the thermodynamically stable 5-alkyl-3-methylphenol by isomerization. The working examples of this DE-A do not report any yields. Instead, what is indicated in the first reaction step are always differently composed mixtures of the theoretically possible isomers; this applies not only to the alkylation products predominantly prepared with propene but also to some reaction products prepared with 1-butene, cyclohexene and styrene.

It is clear that earlier catalysts, such as H$_2$SO$_4$, AlCl$_3$ and H$_3$PO$_4$, which are frequently used in large amounts, present substantial disposal problems. Moreover, it is plain that insoluble catalysts, such as ion exchangers, bleaching earths and molecular sieves, lead in some instances to different products or are successfully usable only on specific substrates.

SUMMARY OF THE INVENTION

A process has now been found for preparing 4-methyl-2-cyclohexylphenol by alkylation of p-cresol with cyclohexanol or cyclohexene, which is characterized in that the alkylation is carried out in the liquid phase in the presence of 1–10% by weight, preferably 2–4% by weight, based on the amount of p-cresol, of a large pore, acidic zeolite by adding the cyclohexanol or cyclohexene to the p-cresol initially introduced.

DETAILED DESCRIPTION OF THE INVENTION

The molar ratio of cyclohexanol or cyclohexene to p-cresol is 1:1–4, preferably 1:1.1–2, particularly preferably 1:1.3–1.8.

The process according to the invention is carried out at a temperature of 140°–200° C., preferably 150°–180° C. The pressure is not critical for the process according to the invention and is merely required in order to keep the bulk of the reactants in the liquid phase; for example, a pressure of 1–10 bar, in many cases of 1–5 bar, is employed. If superatmospheric pressure is employed, the autogenous pressure of the reaction system is the preferred operating pressure.

The use of cyclohexanol in the process according to the invention is associated with the elimination of water of reaction. Since molecular sieves adsorb water, only releasing it completely at temperatures above it was likely that at least some of the channels and pores of the zeolites would be occupied by water if cyclohexanol was used, thereby dramatically cutting the catalytic activity of the zeolites. Surprisingly, this phenomenon was not observed on using cyclohexanol; in addition, cyclohexanol is cheaper, so that the use of cyclohexanol in the process according to the invention constitutes a preferred variant.

In principle, it is possible, if cyclohexanol is used, to leave the water of reaction in the reaction mixture and only to separate it off in the course of the working up. In a preferred variant, however, the water is removed batchwise or continuously from the reaction mixture, which as a person skilled in the art knows is even possible if superatmospheric pressure is employed. This makes it possible to monitor the progress of the reaction. In this variant, the cyclohexanol can be added to the reaction mixture at the rate of water elimination (= rate of the alkylation reaction). If cyclohexene is used, it is added to the reaction mixture at such a rate that there is never any significant cyclohexene reflux.

To carry out the process, a mixture of zeolite and p-cresol is for example heated to the desired reaction temperature with stirring. Cyclohexanol is then added in accordance with the amount of evolved water. In the case of a reaction batch of 2–4 moles of p-cresol, this generally requires a period of 3–6 hours. After all the cyclohexanol has been added, the reaction mixture is stirred at the reaction temperature for a further 2–4 hours. The 4-methyl-2-cyclohexylphenol can then be isolated from the reaction mixture by separating methods known to the person skilled in the art. For instance, it is possible first to remove the zeolite by filtration or centrifuging. However, it is also possible to leave the zeolite at elevated temperature after the reaction has ended and to decant or siphon off the reaction mixture. Such a procedure leaves the repeatedly reusable catalyst in the reaction vessel, in which, after renewed addition of p-cresol and subsequent addition of cyclohexanol, further reaction products can be obtained. The reaction mixture from which the zeolite has been removed can advantageously be worked up further by distillation. The resulting excess p-cresol is recycled.

The procedure if cyclohexene is used is basically the same; it is added, as mentioned above, at such a rate that no significant cyclohexene reflux occurs.

The process according to the invention is carried out in the presence of large pore, acidic zeolites. Zeolites are crystalline alumosilicates with a network of $SiO_4$ and $AlO_4$ tetrahedra. The individual tetrahedra are joined together at the corners via oxygen linkages and form a three-dimensional network which is permeated by channels and voids. The negative charge of the frame work is balanced by the inclusion of exchangeable cations. Zeolites can be represented by the following general formula:

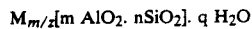
$$M_{m/z}[m\ AlO_2 \cdot nSiO_2] \cdot q\ H_2O \qquad (I)$$

wherein n/m is the Si/Al ratio, $M_{m/z}$ denotes exchangeable cations, where z indicates the valency of the cation, and q indicates the amount of sorbed aqueous phase.

Zeolites of different structures are described, for example, in D. W. Breck, Zeolite Molecular Sieves, John Wiley and Sons Inc., New York, 1974. In such zeolites, the aluminium can furthermore be partly replaced by other trivalent ions for example Fe(III), Ga(III), B(III) and others.

The zeolites according to the invention are large pored, having pore widths of 7 to 9Å.

The zeolites usable according to the invention, furthermore, have an acidic character. This can be obtained by replacing for example the metal cations which the zeolite contains from its natural origin or from its synthesis by ion exchange with acids. Moreover, metal ions can be replaced by the ammonium ion; a subsequent calcination then leads to the release of $NH_3$, leaving a proton-containing zeolite behind. A further possible way of rendering zeolites acidic is to exchange zeolites with ions of valency state of three (for example rare earths, Al, Fe, Ga, In) or of valency state of two (such as, for example, alkaline earths and divalent transition metal cations or divalent main group metal cations) (see P. A. Jacobs, Carboionogenic Activity of Zeolites, Elsevier Scientific Publishing Company, Amsterdam, 1977). Via the degree of exchange ($MeO/Al_2O_3$ $O_3$ or $Me_2O_3/Al_2O_3$, expressed in moles) it is possible to obtain different degrees of acidity in the zeolite.

Zeolite types which are usable according to the invention are for example: zeolite Y, ZSM 12, zeolite L, zeolite Ω, zeolite β, ZSM 20, mordenite, offretite, cancrinite or gmelinite.

Preference is given to using zeolite Y, ZSM 20 and zeolite L. The zeolites can be used in a proton form having degrees of exchange of 5 to 100% not only in respect of the proton but also in a form exchanged with 3-valent ions, such as, for example, rare earths. The zeolites contain either single rare earth cations or different mixtures in degrees of exchange of 5 to 100%, preferably 10 to 100%. It is also possible to use exchange forms with further 3-valent cations, such as, for example, aluminum, iron, chromium, gallium, indium or the like.

It is also possible to use forms exchanged with 2-valent cations, such as, for example, alkaline earth metals, manganese, cobalt, nickel, copper, zinc or cadmium, which can likewise create acidic centres in the zeolite. By variation of the degree of exchange between 5 and 100% it is possible to obtain different degrees of acidity.

Preferred exchange forms are the proton forms within degrees of exchange between 50 and 100%. A further preferred exchange form comprises the large pore zeolites containing rare earths as cation form, in which case it is possible to obtain the preferred acidity level by a degree of exchange of 20 to 90%. It is also possible to use not only La-rich rare earth mixtures but also Ce-rich rare earth mixtures as used in industry. It is also possible to use the pure lanthanides such as, for example, La, Ce, Pr, Nd, Pm, Sm, Eu, Gd and others.

EXAMPLE 1

Preparation of the hydrogen form of zeolite Y 100 g of the sodium form of zeolite Y with a $SiO_2/Al_2O_3$ ratio of 4.8 were mixed with 70 g of an ammonium sulfate solution with a concentration of 132 g $(NH_4)_2SO_4$ per liter. The suspension was stirred for three hours at 90° C. The ion exchange was repeated twice. After the ion exchange the solid was filtered off and washed with water to remove the excess of ammonium sulfate.

The zeolite was dried at 110° C. for three hours. For getting the hydrogen form of the zeolite Y the powder was spread on a tin with a thickness of the layer of one centimeter. The programmed heating was carried out with an increase of 10° C. per minute up to 420° C. At this temperature the zeolite was kept for 60 minutes.

EXAMPLE 2

117 g of cyclohexene were added dropwise to a mixture of 232 g of p-cresol and 6.0 g of H-zeolite Y at 165° C. in the course of 3 hours. The mixture was subsequently stirred at 165° C. for a further 2 hours, and the zeolite was then filtered off. This left 347.6 g of a reaction mixture of the following composition:

| | |
|---|---|
| p-cresol: | 21.0% |
| unknowns: | 0.9% |
| cyclohexyl 4-tolyl ether: | 0.2% |
| 4-methyl-2-cyclohexylphenol: | 71.7% |
| 4-methyl-3-cyclohexylphenol: | 3.8% |
| 4-methyl-2,6-dicyclohexylphenol: | 1.3% |
| 4-methyl-2,5-dicyclohexylphenol: | 1.1% |

The yield of pure 4-methyl-2-cyclohexylphenol was accordingly 249.2 g (92.1% of the theoretical yield based on starting cyclohexene).

EXAMPLE 3

142.5 g of cyclohexanol were added dropwise to a mixture of 232 g of p-cresol and 5.0 g of H-zeolite Y at 165° C. in the course of 3 hours. The resulting water of reaction was continuously separated off. The mixture was stirred at 165° C. for 2 hours, and the zeolite was then filtered off. This left 343.5 g of the reaction mixture of the following composition:

| | |
|---|---|
| p-cresol: | 23.8% |
| unknowns: | 1.3% |
| cyclohxyl 4-tolyl ether: | 0.1% |
| 4-methyl-2-cyclohexylphenol: | 66.9% |
| 4-methyl-3-cyclohexylphenol: | 4.6% |
| 4-methyl-2,6-dicyclohexylphenol: | 2.3% |
| 4-methyl-2,5-dicyclohexylphenol: | 1.0% |

The yield of 4-methyl-2-cyclohexylphenol was accordingly 229.8 g (84.9% of the theoretical yield, based on starting cyclohexanol).

EXAMPLE 4

142.5 g of cyclohexanol were added dropwise to a mixture of 232 g of p-cresol and 5.0 g of rare earthzeolite Y (0.1 rare earth-III-oxide/Al$_2$O$_3$) at 165° C. in the course of 3 hours. The resulting water of reaction was continuously separated off. The mixture was stirred at 165° C. for 2 hours, and the zeolite was then filtered off. This left 345.7 g of the reaction mixture of the following composition:

| | |
|---|---|
| p-cresol: | 19.2% |
| unknowns (4 GC peaks) | 1.0% |
| cyclohexyl 4-tolyl ether | 0.2% |
| 4-methyl-2-cyclohexylphenol | 6.4% |
| 4-methyl-3-cyclohexylphenol | 5.1% |
| 4-methyl-2,6-dicyclohexylphenol | 4.4% |
| 4-methyl-2,5-dicyclohexylphenol | 2.7% |

What is claimed is:

1. In the process for preparing 4-methyl-2-cyclohexylphenol by alkylation of p-cresol with cyclohexanol or cyclohexene in the liquid phase, the improvement which comprises effecting the alkylation in the presence of 1–10% by weight, based on the amount of p-cresol, of a large pore, acidic zeolite by adding the cyclohexanol or cyclohexene to the p-cresol initially introduced.

2. The process of claim 1, wherein the alkylation is carried out in the presence of 2–4% by weight of the zeolite.

3. The process of claim 1, wherein a molar ratio of cyclohexanol or cyclohexene to p-cresol of 1:1–4 is set.

4. The process of claim 3, wherein a molar ratio of cyclohexanol or cyclohexene to p-cresol of 1:1.1–2 is set.

5. The process of claim 4, wherein a molar ratio of cyclohexanol or cyclohexene to p-cresol of 1:1.3–1.8 is set.

6. The process of claim 1, wherein the alkylation is carried out at 140°–200° C.

7. The process of claim 6, wherein the alkylation is carried out at 150°–180° C.

8. The process of claim 1, wherein cyclohexanol is used for the alkylation.

9. The process of claim 8, wherein water formed is removed from the reaction mixture.

10. The process of claim 1, wherein the large pore, acidic zeolites used are those having pore widths of 7 to 9 Å.

11. The process of claim 1, wherein the acidic zeolites used are those which have been exchanged to an extent of 5 to 100% with protons of 2- or 3-valent metal cations.

12. The process of claim 11, wherein the zeolites have been exchanged with protons or 3-valent metal cations.

13. The process of claim 11, wherein the zeolites used have been exchanged to an extent of 10 to 100% with protons.

14. The process of claim 13, wherein the zeolites have been exchanged to an extent of 50–100% with protons.

15. The process of claim 11, wherein the zeolites used have been exchanged to an extent of 20 to 90% with cations of rare earth metals.

16. The process of claim 15, wherein the zeolites used have been exchanged with cations of Ce-rich and/or Larich rare earth mixtures.

17. The process of claim 1, wherein the alkylation is carried out in the presence of 2–4% by weight of the zeolite at 140°–200° C., the molar ratio of cyclohexanol or cyclohexene to p-cresol is 1:1–4, the zeolite having a pore width of 7 to 9 Å and having been exchanged to the extent of 5 to 100% with protons of 2- or 3-valent metal cations.

* * * * *